(12) United States Patent
Van Dyke

(10) Patent No.: US 6,413,236 B1
(45) Date of Patent: Jul. 2, 2002

(54) AUTOMATICALLY RETRACTABLE NEEDLE SAFETY SYRINGE

(76) Inventor: Lewis R. Van Dyke, 1112 Old Modena St., Gastonia, NC (US) 28054

( * ) Notice: Subject to any disclaimer, the term of this patent is extended or adjusted under 35 U.S.C. 154(b) by 109 days.

(21) Appl. No.: 09/598,074

(22) Filed: Jun. 20, 2000

Related U.S. Application Data

(63) Continuation-in-part of application No. 09/415,139, filed on Oct. 8, 1999, now abandoned.

(51) Int. Cl.[7] ............................ A61M 5/00; A61M 5/32; A61M 5/315; A61M 5/31
(52) U.S. Cl. ...................... 604/110; 604/195; 604/198; 604/222; 604/240
(58) Field of Search ............................ 604/93.01, 110, 604/181, 187, 195, 218, 221, 222, 239, 243, 257, 264, 272, 192, 198, 240

(56) References Cited

U.S. PATENT DOCUMENTS

| | | | |
|---|---|---|---|
| 4,838,869 A | 6/1989 | Allard | 604/195 |
| 4,950,241 A | 8/1990 | Ranford | 604/110 |
| 4,966,593 A | 10/1990 | Lennox | 604/198 |
| 5,215,015 A | 6/1993 | Iida | 104/23.1 |
| 5,215,533 A | 6/1993 | Robb | 604/195 |
| 5,334,155 A | 8/1994 | Sobel | 604/110 |
| 5,578,015 A | 11/1996 | Robb | 604/195 |
| 5,658,257 A | 8/1997 | Ryles | 604/195 |
| 5,868,713 A | 2/1999 | Klippenstein | 604/195 |
| 5,964,735 A | 10/1999 | Alexander | 604/195 |
| 5,971,964 A | 10/1999 | Donaldson | 604/195 |
| 6,033,385 A | 3/2000 | Liu | 604/195 |
| 6,036,674 A | 3/2000 | Caizza | 604/195 |
| 6,050,977 A | 4/2000 | Adams | 604/195 |
| 6,193,695 B1 * | 2/2001 | Rippstein, Jr. | 604/195 |

* cited by examiner

Primary Examiner—Michael J. Hayes
(74) Attorney, Agent, or Firm—Dougherty & Clements LLP

(57) ABSTRACT

An automatically retractable needle safety syringe apparatus having an integral safety feature that automatically and immediately retracts the piercing tip end of the needle body after a single use, due to a punch which frictionally engages the foundation of the ferrule and a vacuum created within the syringe body during the process of injecting fluid therefore causing the piercing tip end of the needle body to permanently reside enclosed within the syringe body protectively pressed against the inner surface of the tube thus alleviating needle reuse and accidental needle prickings with contaminated syringe needles and therefore ultimately preventing the transmission of blood-borne pathogens and other diseases by contaminated syringe needles. The method of operation is also disclosed.

17 Claims, 6 Drawing Sheets

AUTOMATICALLY RETRACTABLE NEEDLE SAFETY SYRINGE

CROSS REFERENCE TO RELATED APPLICATION

This application is a continuation-in-part of U.S. patent application Ser. No. 09/415,139 filed Oct. 8, 1999, now abandoned.

FIELD OF THE INVENTION

This invention relates generally to safety syringes, and more specifically to a safety syringe apparatus and method for injecting fluid from a syringe and subsequently automatically and immediately retracting a hollow needle permanently and protectively within the syringe body after a single use.

BACKGROUND OF THE INVENTION

In recent years, the public has become increasingly aware of the health hazards associated with needle reuse and accidental needle prickings. This is true, especially among drug addicts, drug users (e.g., diabetics), medical personnel and healthcare providers. More than twenty blood-borne pathogens can be transmitted by the reuse of needles or accidental needle prickings, just a few of which include human immunodeficiency virus (HIV), acquired immunodeficiency syndrome (AIDS), hepatitis B, hepatitis C, syphilis, malaria, tuberculosis, and herpes.

The problem of spreading blood-borne pathogens through the reuse of needles is significant among drug addicts unwilling or unable to pay for sterile needles. The United States government, having recognized and acknowledged this problem, has attempted to control the reuse of syringe needles among drug addicts by establishing needle exchange programs where drug addicts can obtain free sterile needles in exchange for their contaminated needles. Despite this effort, at least 36% of HIV/AIDS cases and more than 50% of hepatitis B and hepatitis C cases in the United States can be linked to the sharing of needles among drug addicts. With approximately one million people with HIV/AIDS, more than 1.25 million hepatitis B carriers and more than 3.5 million hepatitis C carriers in the United States, the need to curb the practice of sharing needles is great. With more than 1.3 million injection drug users in the United States, the need for syringes having an integral, unremovable and unoverridable safety feature that limits the syringe to only a single use is overwhelming. (tri-ject.net/stats.html).

In addition, the spreading of blood-borne pathogens through the reuse of contaminated needles by drug addicts, drug users, medical personnel and healthcare providers in other countries throughout the world is becoming increasingly prominent. For example, approximately 30% of reported HIV/AIDS cases in Brazil, Chile, Uruguay, Paraguay and Argentina are directly related to the sharing of contaminated needles among drug addicts. Nearly 74% of injection drug addicts in Spain are HIV infected. Approximately 70% of the HIV cases reported in China are directly linked to the sharing of contaminated needles. In eastern European countries, 80% of injection drug addicts admit to sharing contaminated needles. Approximately 43% of the HIV/AIDS cases reported in Poland and Yugoslavia are linked to the sharing of contaminated needles among drug addicts. Furthermore, It is estimated that approximately 22 million people worldwide are living with HIV or AIDS. Unfortunately, in many countries, especially third world countries, sterile syringes are simply unavailable due to economic reasons. (www.vanishpoint.com/needlestick.html).

Although approximately one million accidental needle prickings are reported by healthcare workers annually, at least three million accidental needle prickings occur each year that subsequently go unreported. Various studies estimate that out of all the needle pricking injuries that occur to nurses, approximately 40% to 53% go unreported. Various studies also estimate that out of all the needle pricking injuries that occur to laboratory technicians, approximately 92% go unreported. Various studies further estimate that out of all the needle pricking injuries that occur to physicians, approximately 70% to 95% go unreported. (www.osha-slc.gov/SLTC/needlestick/saferneedle devices/saferneedledevices.html).

In 1997, the Centers for Disease Control and Prevention (CDC) sponsored a study which found that approximately 76% of needle pricking injuries could be avoided by using safety needles. As a result, needle legislation has now been introduced in approximately twenty-five states and in the District of Columbia. In fact, such safety needle legislation has already been signed into law in a number of states including California, Texas, Tennessee, New Jersey and Maryland. In addition, the Occupational Safety and Health Administration (OSHA) has promulgated a Blood-borne Pathogens Standard requiring employers to evaluate the effectiveness of existing controls designed to minimize or eliminate employee occupational exposure and to review the feasibility of instituting more advanced controls. Furthermore, the Food and Drug Administration (FDA), in an effort to protect health care workers, has set forth guidelines suggesting specific features that a safety syringe should possess. These include a safety feature that is not only simple and self evident to operate, thus requiring little or no additional training to use effectively, but also a safety feature that is an integral part of the apparatus. In other words, the guidelines suggest that the safety feature itself be unremovable and utilization of the safety feature be unavoidable. (www.osha-slc.gov/SLTC/needle stick/saferneedledevices/saferneedledevices.html; www.seiu.org).

As a result of the foregoing state legislation and agency guidelines, a great amount of time, effort and money has been invested by syringe manufacturers in developing syringes with safety needle designs. Presently, there are at least 250 types of safety syringes. However, the safety syringes that currently exist have been criticized for generally being too expensive to manufacture and having a safety feature that is not an integral part of the safety syringe. Another criticism includes safety syringes that are not economically feasible because operation of the safety feature is not self evident and therefore additional training is required to use the apparatus effectively. Additionally, the safety feature of at least one safety syringe is simply ineffective at preventing the transmission of blood-borne pathogens due to "reflux" blood contamination.

Of the current safety syringes, safety syringes using a spring mechanism are the most common for automatically retracting a hollow needle after injecting a fluid. However, these safety syringes are typically more expensive because of the required incorporation of additional materials for manufacture. Standard or conventional hypodermic needle syringes typically cost from five to seven cents each. On the other hand, the median increase in cost for a safety syringe is approximately thirty cents or more. At first glance, this minimal cost increase does not seem significant. However, after considering the thousands, if not millions, of needles used each year, the resultant increase in annual cost for utilizing the more expensive safety syringe is unfortunately excessive.

Another type of safety syringe is a syringe using a protective shield that slides and locks over the needle to protectively encase the piercing tip. However, the protective shield is not an integral part of the safety syringe. Because the protective shield slides manually over the needle, this safety feature may be overridden by a person who inadvertently or purposely fails to slide the shield over the needle thereby exposing a contaminated and potentially infectious piercing tip. Additionally, the protective shield requires two hands to slide the shield over the needle to encase the syringe needle. As a result, a person's hands may slip while sliding the shield and subsequently be pricked with the exposed and contaminated piercing tip.

Another type of safety syringe is a needleless jet injector that shoots a pinpoint jet of fluid through the skin at extremely high velocities. However, this safety syringe is not economically feasible because operation is not self evident and, therefore, costly time consuming training is required to use the apparatus effectively. Additionally, the needleless jet injector has been linked to causing hepatitis B infections resulting from "reflux" blood contamination of the injector heads from the previous injection. One approach is to provide proper cleaning and maintenance of the injector heads between injections, however this is time consuming and is not failsafe at preventing subsequent transmission of infectious blood-born pathogens. Another approach is to provide needleless jet injectors with nozzles and fluid chambers that can both be discarded after each injection. However, these safety features are mere accessories to, and are not built-in as integral parts of the apparatus. Therefore, the safety features of the needleless jet injector could be removed or even overridden by not utilizing a sterile, unused nozzle and/or fluid chamber attachments.

Therefore a need exists for an effective and efficient, inexpensive safety syringe that is simple and self evident to operate and integrally comprises a safety feature having a hollow needle that protectively retracts automatically after a single injection. Further needed is a safety syringe that alleviates needle reuse and accidental needle prickings with contaminated syringe needles and therefore ultimately assists in preventing the transmission of blood-borne pathogens such as HIV/AIDS, hepatitis B and hepatitis C via contaminated syringe needles.

SUMMARY OF THE INVENTION

The present invention is a safety syringe apparatus and method for injecting fluid from a syringe and subsequently automatically and immediately retracting a hollow needle permanently and protectively within the syringe body after a single use. The present invention prevents needle reuse and accidental needle prickings with contaminated syringe needles.

The invented apparatus includes a syringe body having a plunger and a needle body, both of which are slidably disposed and partially positioned within the syringe body. The syringe body includes a shaft seal at a first end of the syringe body and a variable vacuum compartment. The plunger includes a shaft, a piston seal attached proximally to one end of the shaft and a punch located at the end of the shaft. The shaft of the plunger is slidably engageable with the shaft seal of the syringe body. The piston seal of the plunger is slidably disposed within the syringe body. The syringe body between the shaft seal and the piston seal defines the variable vacuum compartment. The needle body is temporarily attached to a second end, opposing the first end, of the syringe body and includes a piercing tip end attached to a ferrule.

During an injection stroke of a single injection of fluid, a vacuum is created within the variable vacuum compartment as a result of an increase in volume within the variable vacuum compartment without a corresponding influx of air molecules and fluid molecules into the variable vacuum compartment, due to the shaft seal and the piston seal being substantially air tight and fluid tight. At the end of the injection stroke, the punch frictionally engages the ferrule. The needle is immediately and automatically withdrawn within the syringe body as a result of the vacuum created within the variable vacuum compartment during the injection stroke. The needle body is withdrawn into the syringe body such that the piercing tip end permanently resides enclosed within and protectively pressed against the syringe body. This alleviates needle reuse and accidental needle prickings and, therefore, ultimately prevents the transmission of blood-borne pathogens and other diseases by contaminated syringe needles.

The invented safety syringe apparatus is efficient and effective at preventing the transmission of blood-borne pathogens and other diseases through needle reuse or accidental needle prickings with contaminated syringe needles. The safety syringe is also inexpensive to manufacture relative to the cost of manufacturing standard or conventional hypodermic needle syringes. In addition, the safety feature of the invented apparatus is simple and self evident to operate and therefore requires no additional training to use the apparatus efficiently and effectively.

This safety feature is an integral part of the invented safety syringe apparatus, meaning that the safety feature is built-in as a necessary, inherent and integral part of the apparatus. Because this safety feature is not a mere accessory which might be removed, circumvented or overridden after a single use, the piercing tip end permanently resides enclosed within and protectively pressed against the syringe body therefore providing a protective barrier between the person's hands and the contaminated needle. Furthermore, this safety feature goes into effect automatically and immediately after a single use and remains in effect during disposal, thus alleviating needle reuse and accidental needle prickings with contaminated syringe needles. Therefore, the safety feature ultimately prevents the transmission of blood-borne pathogens such as HIV/AIDS, hepatitis B, hepatitis C and other diseases by needle reuse and accidental needle prickings with contaminated syringe needles.

OBJECTS OF THE INVENTION

The principal object of the present invention is to provide an automatically retractable needle safety syringe apparatus that injects fluid from a syringe and subsequently automatically and immediately retracts the piercing tip end of a hollow needle permanently within the safety syringe body, protectively pressed against the inner surface of the tube, after a single use thus preventing the transmission of blood-borne pathogens, such as HIV/AIDS, hepatitis B, hepatitis C and other diseases, via needle reuse and accidental needle prickings with contaminated syringe needles.

Another object of the present invention is to provide a method of automatically and immediately retracting the piercing tip end of a hollow needle permanently within the safety syringe body, protectively pressed against the inner surface of the tube, after a single use thus preventing the transmission of blood-borne pathogens, such as HIV/AIDS, hepatitis B, hepatitis C and other diseases, via needle reuse and accidental needle prickings with contaminated syringe needles.

Another object of the present invention is to provide a safety syringe apparatus that permanently prevents needle reuse or accidental needle prickings with contaminated syringe needles by providing a protective barrier between the hands and the hollow needle automatically and immediately after a single use and during disposal.

Another object of the present invention is to provide an automatically and immediately retractable needle safety syringe apparatus that is both efficient and effective at preventing the transmission of blood-borne pathogens and other diseases through needle reuse or accidental needle prickings with contaminated syringe needles.

Another object of the present invention is to provide an automatically and immediately retractable needle.safety syringe apparatus that is simple and inexpensive to manufacture, relative to the cost of manufacturing standard or conventional hypodermic needle syringes.

Another object of the present invention is to provide an automatically and immediately retractable needle safety syringe apparatus that is simple and self evident to operate and therefore requires no additional training to use the apparatus effectively and efficiently.

Another object of the present invention is to provide an automatically and immediately retractable needle safety syringe apparatus having a safety feature that is an integral part of the safety syringe, meaning that the safety feature is built-in as a necessary, inherent and integral part of the apparatus and is therefore not merely an accessory which might be removed, circumvented or overridden.

BRIEF DESCRIPTION OF THE DRAWINGS

The foregoing and other objects will become more readily apparent by referring to the following detailed description and the appended drawings in which.

DETAILED DESCRIPTION

The present invention is a safety syringe apparatus and method for injecting fluid from a syringe and subsequently automatically and immediately retracting a hollow needle permanently and protectively within the syringe body after a single use. The present invention prevents needle reuse and accidental needle prickings with contaminated syringe needles.

Figure 1:
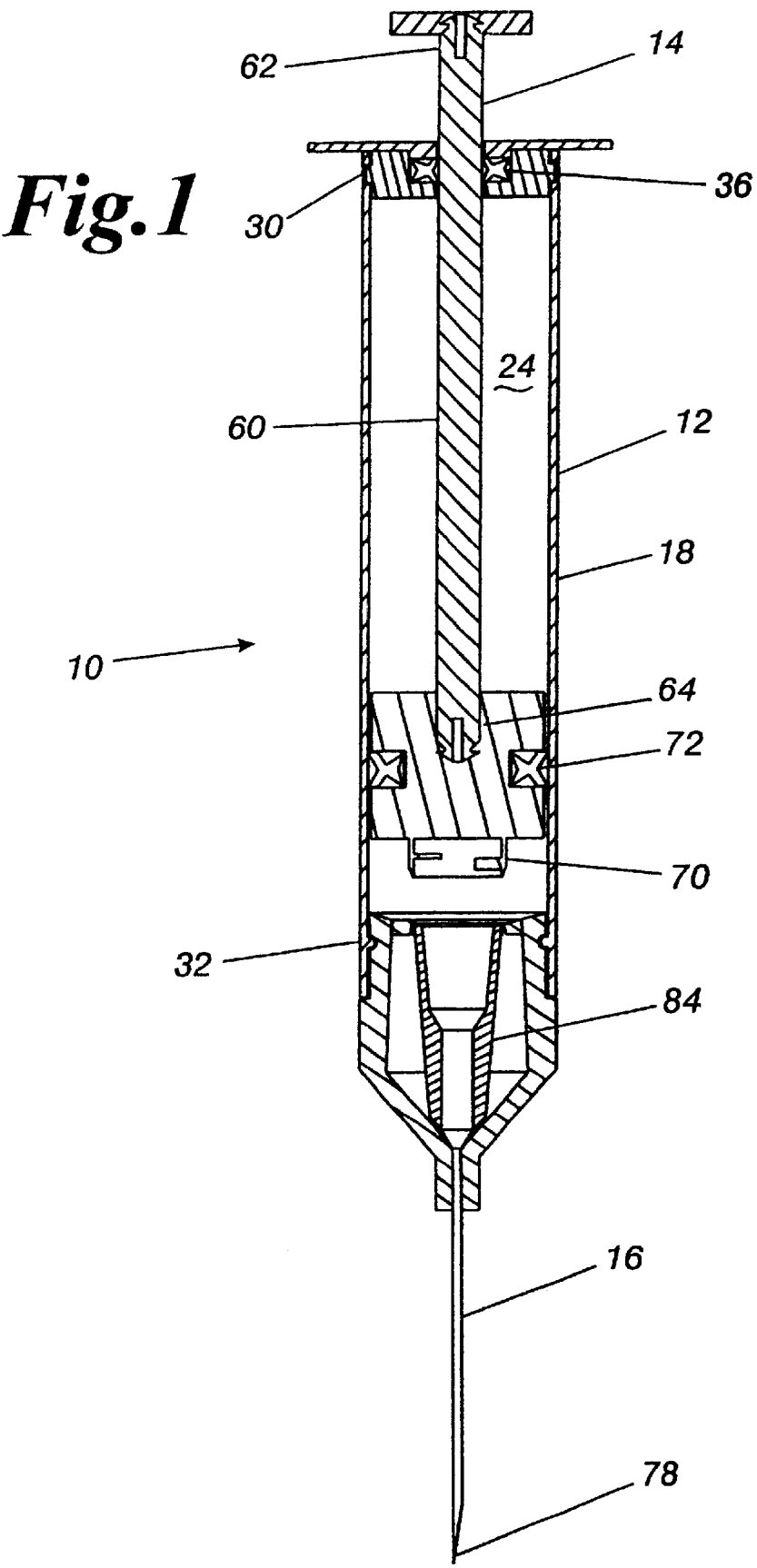
FIG. 1 is a cross sectional view of a safety syringe apparatus in accordance with the present invention.

FIG. 1 is a cross sectional view of a safety syringe apparatus 10 in accordance with the present invention. An embodiment of the invented safety syringe apparatus 10, as shown in FIG. 1, includes a syringe body 12, a plunger 14 and a needle body 16. Both the plunger 14 and the needle body 16 are slidably disposed and partially positioned within the syringe body 12. The syringe body 12 is a tube 18 having two opposing ends 30, 32 and includes a shaft seal 36 and a variable vacuum compartment 24 at one end 30 of the syringe body 12. The plunger 14 includes a shaft 60 having a thumb end 62 and a piston end 64 opposing the thumb end 62, a piston seal 72 attached proximally to the piston end 64 of the shaft 60 and a punch 70 attached to the piston end 64 of the shaft 60. The shaft seal 36 and piston seal 72 maintain a substantially air tight and fluid tight seal between the shaft 60 and the syringe body 12 as the plunger 14 is displaced into and out of the syringe body 12. The syringe body 12 between the shaft seal 36 and the piston seal 72 defines the variable vacuum compartment 24. The needle body 16 is temporarily attached to a second end 32 of the syringe body and includes a piercing tip end 78 attached to a ferrule 84.

Figure 2:
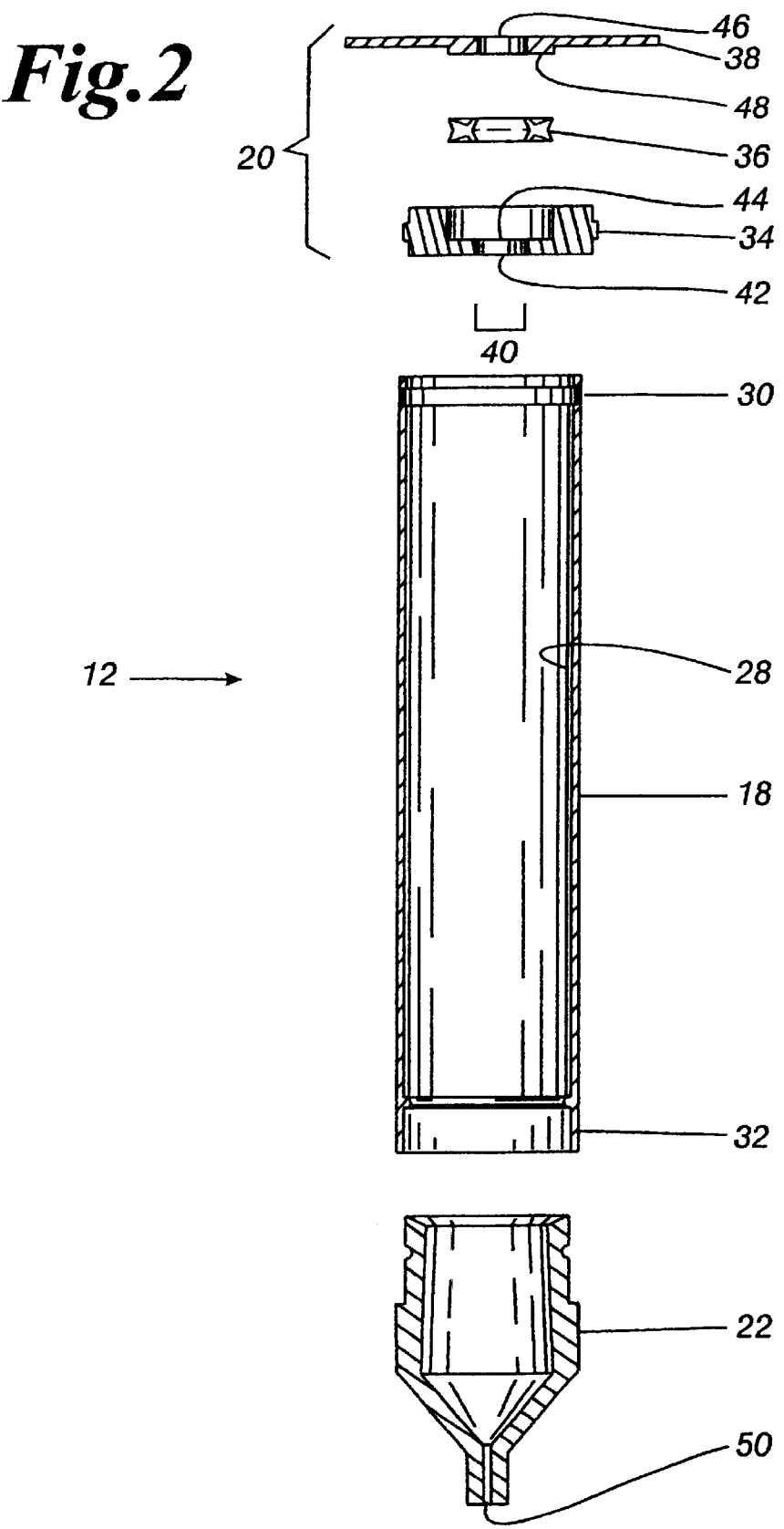
FIG. 2 is an exploded cross sectional view of the syringe body shown in FIG. 1.

FIG. 2 is an exploded cross sectional view of the syringe body 12. The tube 18 includes an inner surface 28, a shaft seal attachment end 30 and a needle attachment end 32 opposing the shaft seal attachment end 30. The inner surface 28 of the tube 18 extends within and along the tube 18 between the shaft seal attachment end 30 and the needle attachment end 32. As shown in FIG. 2, the syringe body 12 additionally includes a shaft seal attachment 20 insertably attachable to the shaft seal attachment end 30 for receiving the previously mentioned plunger 14.

The shaft seal attachment 20 includes an attachment base 34, a shaft seal 36, an attachment head 38 and a shaft orifice 40 formed there through. The attachment base 34 has a shaft opening 42 for receiving the previously mentioned shaft 60 and a shaft seal annular groove 44 for receiving the shaft seal 36. The attachment head 38 is equipped with a shaft opening 46 and a shaft seal annular groove tab 48 that couples the attachment head 38 to the attachment base 34 so that the shaft seal 36 is interposed between the attachment head 38 and the attachment base 34. The shaft seal attachment 20 is assembled by coupling the attachment head 38 to the attachment base 34. Once assembled, the shaft orifice 40 of the shaft seal attachment 20 is formed by the shaft opening 42 of the attachment base 34, the shaft opening 46 of the attachment head 38 and the shaft seal 36. During assembly, the shaft seal attachment 20 is attached to the tube 18 by inserting the shaft seal attachment 20 into the shaft seal attachment end 30 of the tube 18.

The syringe body 12 additionally includes a needle attachment 22 insertably attachable to the needle attachment end 32 for receiving the previously mentioned needle body 16. The needle attachment 22 includes a needle receiving conduit 50. During assembly, the needle attachment 22 is attached to the tube 18 by inserting the needle attachment 22 into the needle attachment end 32 of the tube 18.

Figure 3:
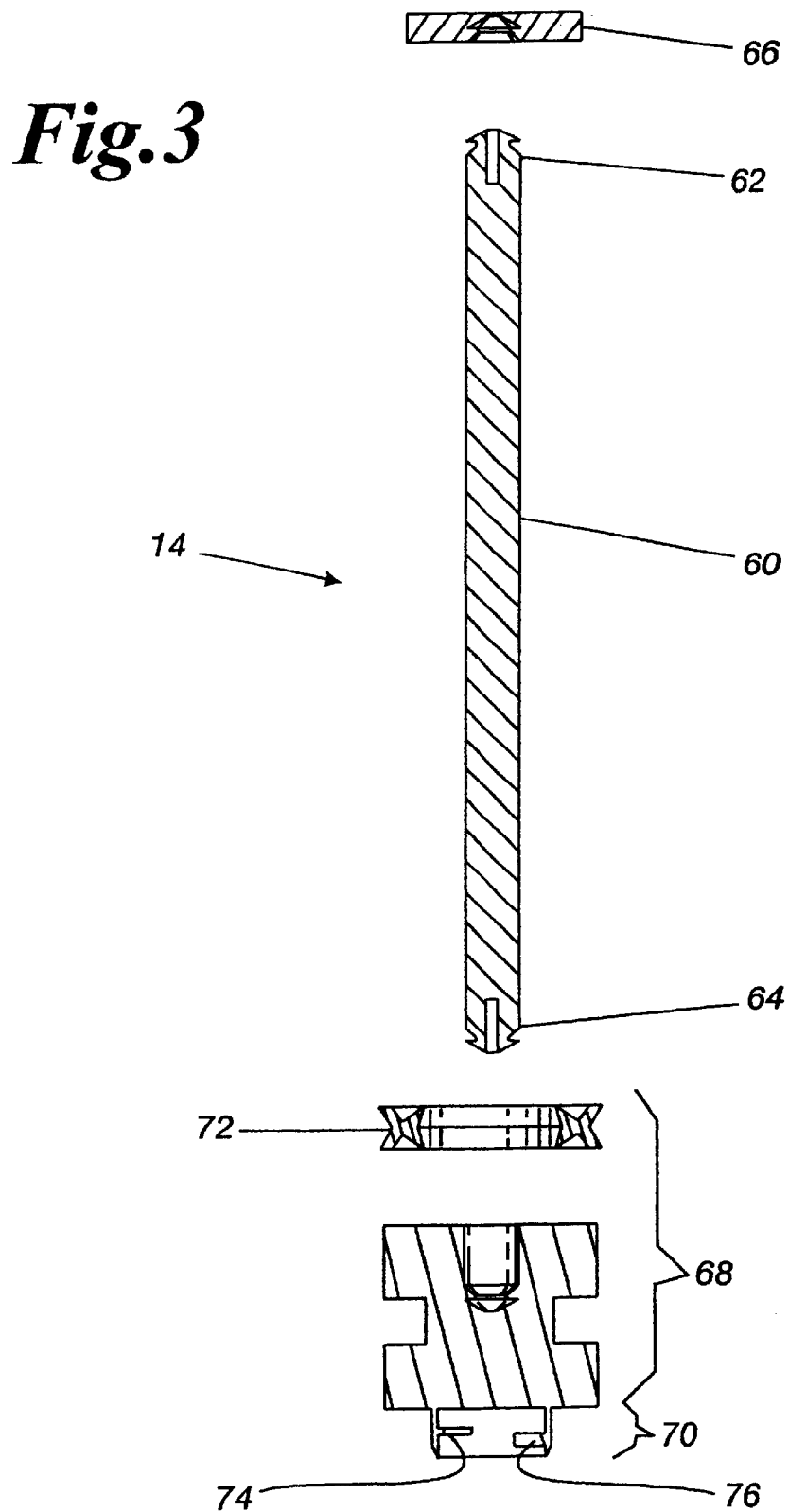
FIG. 3 is an exploded cross sectional view of the plunger shown in FIG. 1.

FIG. 3 is an exploded cross sectional view of the plunger 14 shown in FIG. 1. The plunger 14 includes the previously mentioned shaft 60, thumb end 62 and piston end 64 opposing the thumb end 62, and also includes a thumb platform 66 attached to the thumb end 62, a piston 68 attached to the piston end 64 and the previously mentioned punch 70 attached to the piston end 64 and positioned adjacent the piston 68. In an alternative embodiment, the punch 70 is attached to the piston 68 and is positioned adjacent the piston end 64 of the plunger 14. The piston 68 is equipped with a piston seal 72 attached proximally to the piston end 64 of the plunger 14. The shaft 60 is preferably a solid elongate cylindrical tube shape. In an alternative embodiment, the shaft 60 is substantially hollow to provide additional volume within the previously mentioned variable vacuum compartment 24 for creating a vacuum while maintaining requisite structural integrity of the shaft 60. In another alternative embodiment, the shaft 60 is an elongate cross shape in contrast with the solid elongate cylindrical tube shape as shown in FIG. 3.

Figure 4:
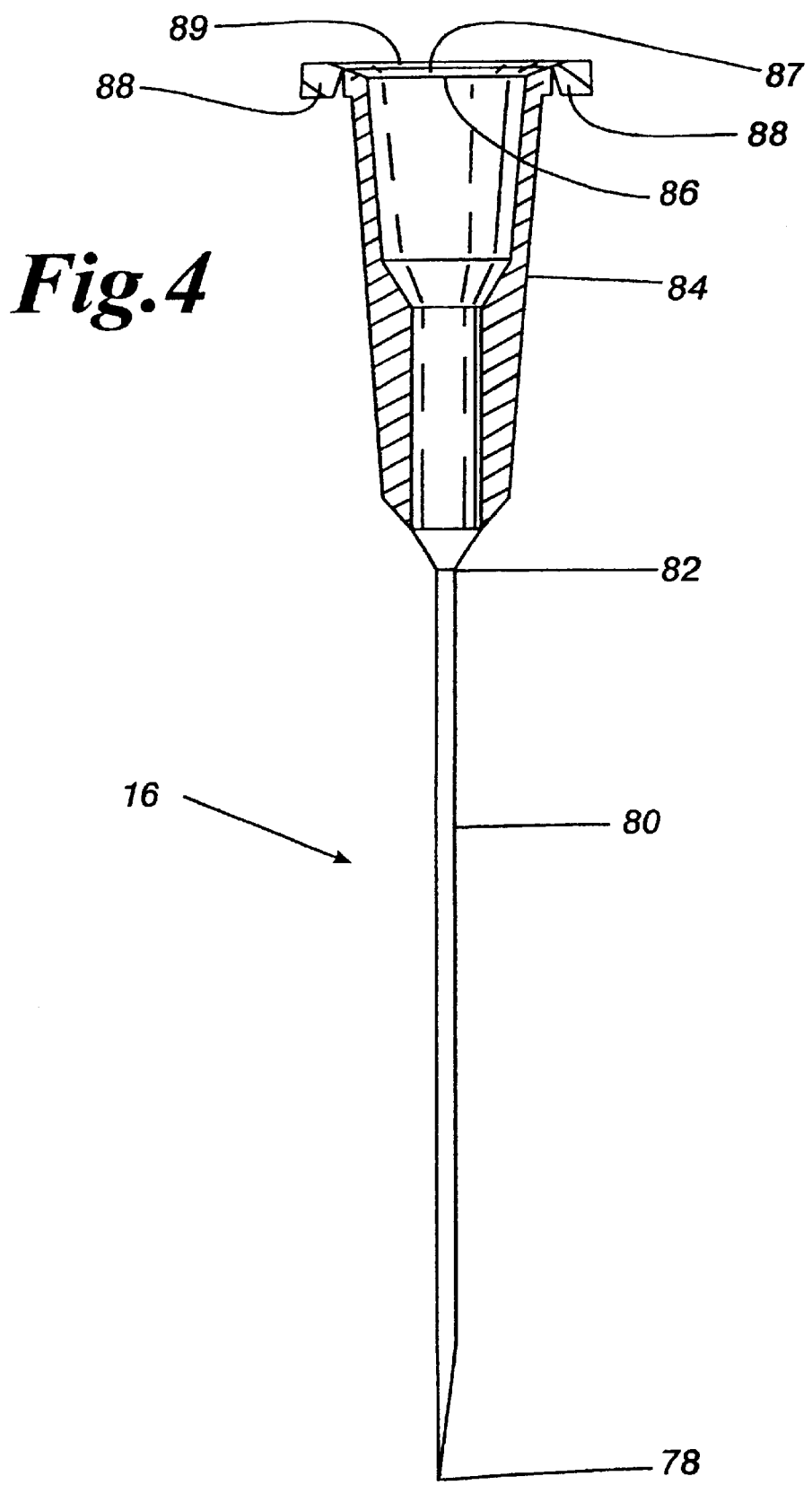
FIG. 4 is a cross sectional view of the needle body shown in FIG. 1.

FIG. 4 is a cross sectional view of the needle body 16 shown in FIG. 1. The needle body 16 includes a hollow capillary channel 80 having the previously mentioned piercing tip end 78 and a ferrule end 82 opposing the piercing tip end 78, and the previously mentioned ferrule 84 attached to the ferrule end 82 of the hollow capillary channel 80. The ferrule 84 has a foundation 86 and a grommet 88. The foundation 86 has a surface 87. The grommet 88 has a surface 89 that is temporarily and peripherally attached to the surface 87 of the foundation 86 of the ferrule 84.

Figure 5:
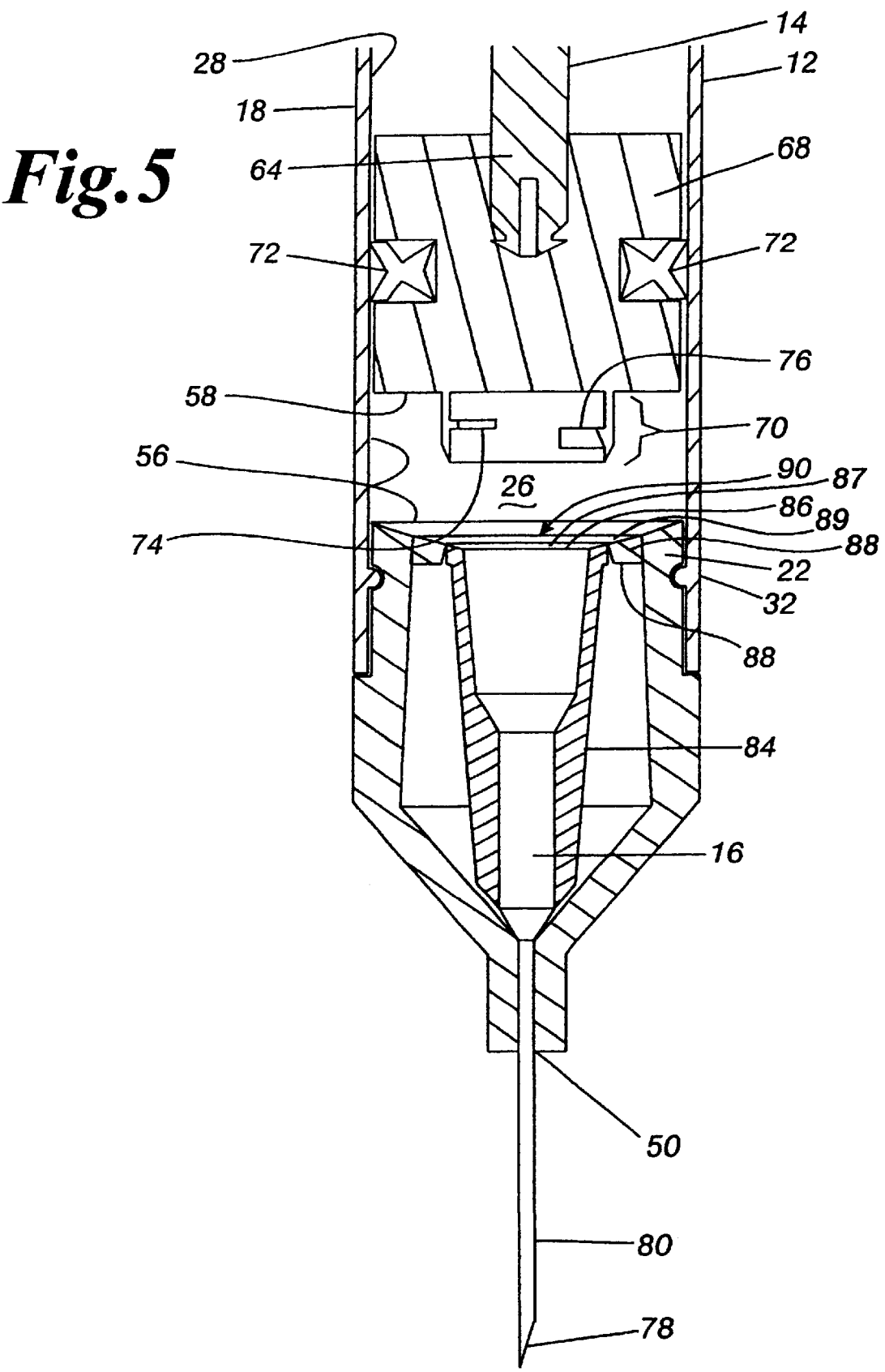
FIG. 5 is a detailed enlarged cross sectional view of a portion of the safety syringe apparatus shown in FIG. 1.

FIG. 5 is a detailed enlarged cross sectional view of a portion of the safety syringe apparatus 10 shown in FIG. 1. The needle body 16 is temporarily attached to the needle attachment 22 of the syringe body 12. In a preferred embodiment, the surface 89 of the grommet 88 temporarily and peripherally attaches the surface 87 of the foundation 86 of the ferrule 84 to the needle attachment 22 of the syringe body 12 to form a surface 90 that is slightly concave. In this alternative embodiment, the resulting surface 90 may otherwise be concave or substantially flat. In an alternative embodiment, the surface 89 of the grommet 88 temporarily and peripherally attaches the surface 87 of the foundation 86 of the ferrule 84 to the inner surface 28 of the tube 18 to form a surface 90 that is slightly concave. In this alternative embodiment, the resulting surface 90 may otherwise be concave or substantially flat.

The tube 18 of the syringe body 12 also has a fluid compartment 26 defined by a stationary surface 56 and a surface 58. The stationary surface 56 of the fluid compartment 26 includes the slightly concave surface 90 and the inner surface 28 of the tube 18 extending within and along the tube 18 between the needle attachment 22 and the surface 58. The surface 58 of the fluid compartment 26 includes the piston 68. The piston 68 is slidably disposed, via the piston seal 72, against the inner surface 28 of the tube 18 while the plunger 14 is displaced into and out of the syringe body 12.

The punch 70 is attached to the piston end 64, positioned adjacent the piston 68 and protrudes toward the needle attachment 22 when the apparatus 10 is assembled. The punch 70 is a substantially hollow cylinder. In a preferred embodiment the punch 70 is equipped with an upper proximal block tab 74 extending around less than about one-half of the circumference of the substantially hollow cylinder, and a lower distal wedge tab 76 extending around less than about one-half of the circumference of the substantially hollow cylinder and located opposite the upper block tab 74. The hollow capillary channel 80 and the piercing tip end 78 of the needle body 16 are slidably disposed within the needle receiving conduit 50 of the needle attachment 22.

Figure 6:
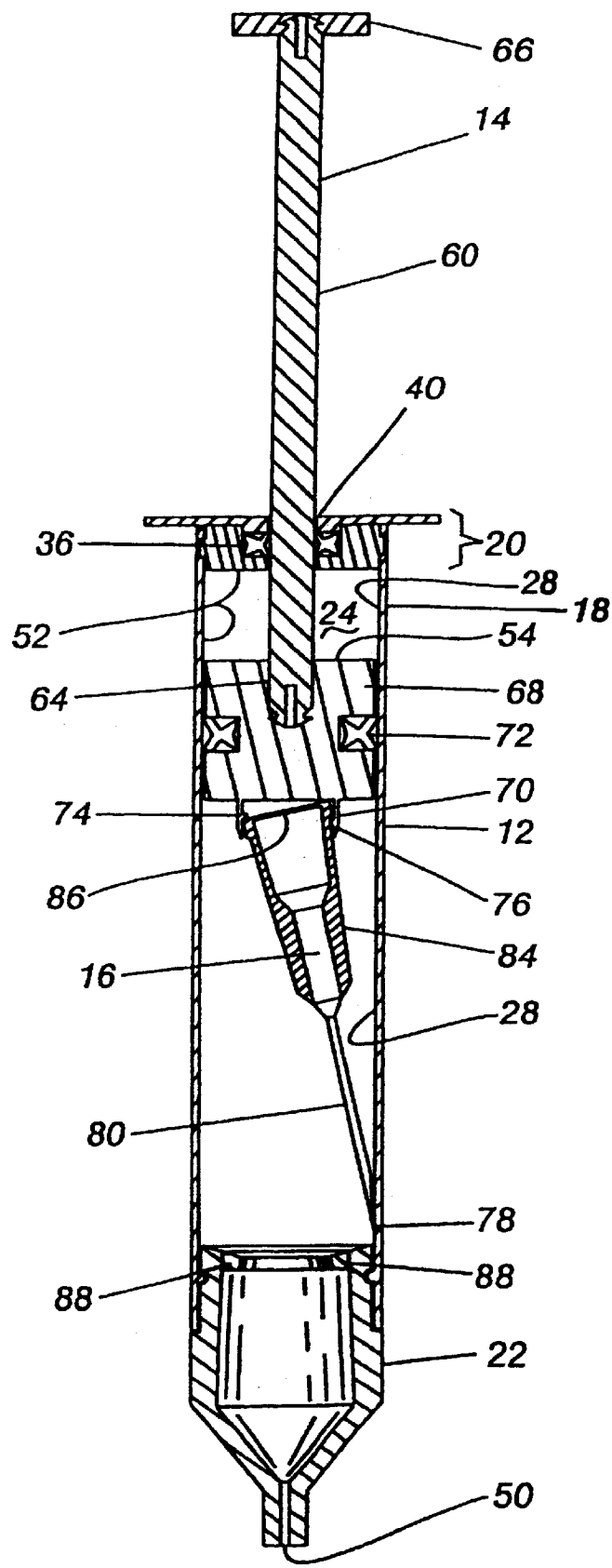
FIG. 6 is a cross sectional view of the needle body permanently residing enclosed within the syringe body and protectively pressed against the inner surface of the syringe body immediately after a single use in accordance with the present invention.

FIG. 6 is a cross sectional view of the needle body 16 permanently residing enclosed within the syringe body 12 and protectively pressed against the inner surface 28 of the syringe body 12 immediately after a single use in accordance with the present invention. The punch 70 frictionally engages the foundation 86 of the ferrule 84, with the upper block tab 74 and the lower wedge tab 76, and the needle body 16 permanently resides enclosed within the syringe body 12 and protectively pressed against the inner surface 28 of the syringe body 12 automatically and immediately after an injection stroke of a single use. The variable vacuum compartment 24 of the syringe body 12 is defined by a stationary surface 52 and a piston surface 54 of the piston 68. The stationary surface 52 of the variable vacuum compartment 24 includes the shaft seal attachment 20 and the inner surface 28 of the tube 18 extending within and along the tube 18 between the shaft seal attachment 20 and the piston surface 54. The shaft 60 is positioned within the shaft orifice 40 of the shaft seal attachment 20 and is slidably engageable with the shaft seal 36. The diameter of the shaft 60, is small enough to provide sufficient volume within the variable vacuum compartment 24 necessary for creating a vacuum, while large enough to provide the requisite structural integrity to the shaft 60. The piercing tip end 78 of the needle body 16 as well as the hollow capillary channel 80 of the needle body 16 are slidably disposed within the needle receiving conduit 50 of the needle attachment 22.

In operation, as shown in FIG. 5 and FIG. 6, during an injection stroke of a single injection of fluid, a vacuum is created within the variable vacuum compartment 24 as a result of an increase in volume within the variable vacuum compartment 24 without a corresponding influx of air molecules, due to the shaft seal 36 and the piston seal 72 creating and maintaining a substantially air tight and fluid tight seal between not only the shaft 60 and the shaft seal attachment 20, but also the piston 68 and the inner surface 28 of the tube 18. At the end of the injection stroke, the upper block tab 74 and the lower wedge tab 76 of the punch 70 frictionally engage the foundation 86 of the ferrule 84. The needle body 16 is immediately and automatically withdrawn within the syringe body 12 as a result of the vacuum created within the variable vacuum compartment 24 during the injection stroke. The needle body 16 is withdrawn into the syringe body 12 such that the piercing tip end 78 permanently resides enclosed within and protectively pressed against the tube 18. This alleviates needle reuse and accidental needle prickings and, therefore, ultimately prevents the transmission of blood-borne pathogens and other diseases by contaminated syringe needles.

More specifically, as shown in FIG. 5 and FIG. 6, to effectuate an intake of fluid into the fluid compartment 26 of the syringe body 12, the thumb platform 66 of the plunger 14 should first be depressed by thrusting the thumb platform 66 partially towards the slightly concave surface 90 to remove a majority of the air present within the fluid compartment 26. During this depression, the piston 68 of the plunger 14 is forced to slide, via the piston seal 72 of the piston 68, against the inner surface 28 of the tube 18 partially towards the slightly concave surface 90. Because the shaft seal 36 of the shaft seal attachment 20 and the piston seal 72 of the piston 68 are substantially air tight and fluid tight, a corresponding influx of air molecules and fluid molecules into the variable vacuum compartment 24 of the syringe body 12 is prevented. As a result, the volume within the variable vacuum compartment 24 is increased without a corresponding influx of air molecules or fluid molecules therefore creating a vacuum within the variable vacuum compartment 24. Secondly, while the thumb platform 66 remains forceably depressed, the piercing tip end 78 of the needle body 16 is submerged into a fluid present within a fluid container. Once the piercing tip end 78 is submerged within the fluid, the thumb platform 66 is allowed to move, as a result of the vacuum created within the variable vacuum compartment 24, away from the needle attachment 22 thus effectuating a withdraw of a desired amount of fluid from a fluid container into the fluid compartment 26 of the syringe body 12.

Now that the fluid is located within the syringe body 12, any residual air must be removed prior to injection. By inverting the safety syringe apparatus so that the piercing tip end 78 is substantially vertical, the fluid, which is more dense than the residual air, is pulled by gravity towards the piston 68 of the plunger 14 while the residual air rises away from the piston 68 towards the slightly concave surface 90. While maintaining the safety syringe apparatus in this substantially vertical position the thumb platform 66 of the plunger 14 is slightly depressed by thrusting the thumb platform 66 only partially towards the slightly concave surface 90, just enough to remove all of the residual air present within the syringe body 12.

As shown in FIG. 5 and FIG. 6, during an injection stroke of a single injection of fluid, the thumb platform 66 of the plunger 14 is depressed by thrusting the thumb platform 66 towards the slightly concave surface 90 to remove substantially all of the fluid contained within the syringe body 12. During this depression, a vacuum is created, as previously discussed herein above, within the variable vacuum compartment 24. At the end of the injection stroke, the punch 70 of the plunger 14 penetrates the slightly concave surface 90, severs the surface 89 of the grommet 88 of the ferrule 84 and frictionally engages the foundation 86 of the ferrule 84 with the upper block tab 74 and lower wedge tab 76 of the punch 70. The foundation 86 of the ferrule 84, which is now frictionally engaged by the punch 70, is immediately and automatically retracted into the syringe body 12 as a result of the vacuum created within the variable vacuum compartment 24. This causes the piercing tip end 78 of the needle body 16 to permanently reside enclosed within the syringe body 12 and protectively pressed against the inner surface 28 of the tube 18 automatically and immediately after a single injection of fluid. Thus, the invented syringe apparatus 10 prevents needle reuse and accidental needle prickings and therefore ultimately alleviates the transmission of blood-borne pathogens and other diseases by contaminated syringe needles.

In one embodiment as shown in FIG. 5 and FIG. 6, the automatically retractable needle safety syringe apparatus 10 has a syringe body 12 that is transparent to allow visibility of the injection fluid within the fluid compartment 26. The safety syringe apparatus 10 has a capacity for injecting at least about 1 cc of fluid, and preferably from about 3 cc to about 10 cc of fluid, to create the requisite amount of vacuum within the variable vacuum compartment 24 for withdrawing the needle body 16 into the syringe body 12. The piercing tip end 78 then permanently resides enclosed within the syringe body 12 and protectively pressed against the inner surface 28 of the tube 18.

In an alternative embodiment, the piercing tip end 78 permanently and protectively resides enclosed within the fluid compartment 26 of the syringe body 12, without being pressed against the inner surface 28 of the tube 18, automatically and immediately after a single injection of fluid.

Summary of the Achievement of the Objects of the Invention

From the foregoing, it is readily apparent that I have invented an automatically retractable needle safety syringe apparatus that provides for injecting fluid from a syringe and subsequently automatically and immediately retracting the piercing tip end of a hollow needle permanently within the safety syringe body, protectively pressed against the inner surface of the tube, after a single use thus preventing the transmission of blood-borne pathogens, such as HIV/AIDS, hepatitis B, hepatitis C and other diseases, via needle reuse and accidental needle prickings with contaminated syringe needles. It is also readily apparent that I have invented an automatically retractable needle safety syringe apparatus that provides for a method of automatically and immediately retracting the piercing tip end of a hollow needle permanently within the safety syringe body, protectively pressed against the inner surface of the tube, after a single use thus preventing the transmission of blood-borne pathogens, such as HIV/AIDS, hepatitis B, hepatitis C and other diseases, via needle reuse and accidental needle prickings with contaminated syringe needles.

The present invention also provides a safety syringe apparatus that permanently prevents needle reuse or accidental needle prickings with contaminated syringe needles by providing a protective barrier between the hands and the hollow needle automatically and immediately after a single use and during disposal. The present invention also provides an automatically and immediately retractable needle safety syringe apparatus that is both efficient and effective at preventing the transmission of blood-borne pathogens and other diseases through needle reuse or accidental needle prickings with contaminated syringe needles. The present invention also provides an automatically and immediately retractable needle safety syringe apparatus that is simple and inexpensive to manufacture, relative to the cost of manufacturing standard or conventional hypodermic needle syringes. The present invention also provides an automatically and immediately retractable needle safety syringe apparatus that is simple and self evident to operate and therefore requires no additional training to use the apparatus effectively and efficiently. The present invention also provides an automatically and immediately retractable needle safety syringe apparatus having a safety feature that is an integral part of the safety syringe, meaning that the safety feature is built-in as a necessary, inherent and integral part of the apparatus and is therefore not merely an accessory which might be removed, circumvented or overridden.

It is to be understood that the foregoing description and specific embodiments are merely illustrative of the best mode of the invention and the principles thereof, and that various modifications and additions may be made to the apparatus by those skilled in the art, without departing from the spirit and scope of this invention which is intended to be limited only by the scope of the appended claims.

What is claimed is:

1. An automatically retractable needle safety syringe apparatus, comprising:
   a syringe body having seal means on an end thereof;
   a needle body having attachment means for temporarily attaching said needle body to said syringe body; and
   a plunger having seal means and punch means, said seal means of said plunger and said seal means of said syringe body together creating a vacuum within said syringe body, said punch means of said plunger for engaging and withdrawing said needle body within said syringe body.

2. An automatically retractable needle safety syringe apparatus, comprising:
   a syringe body having a pair of opposing ends and a variable vacuum compartment within said syringe body, said variable vacuum compartment located at a first end of said syringe body;
   a needle body having a surface temporarily attached to said syringe body at a second end of said syringe body; and a plunger slidably engageable with said syringe body having a punch attached to said plunger, said punch having a piercing edge for piercing said surface of said needle body and a pair of internal, longitudinally offset tabs for frictionally engaging said needle body.

3. A safety syringe apparatus according to claim 2, wherein said pair of internal longitudinally offset tabs of said punch comprise:

a first internal proximal tab shaped to press against said needle body at the end of the injection stroke; and a second internal distal tab shaped to engage said needle body at the end of the injection stroke.

4. A safety syringe apparatus according to claim 3, wherein said syringe body further comprises:

a shaft seal attachment end;

a needle attachment end opposing said shaft seal attachment end; and a shaft seal insertably attachable into said shaft seal attachment end.

5. A safety syringe apparatus according to claim 4, wherein said needle body is temporarily attached to said needle attachment end of said syringe body, said needle body further comprises:

a ferrule; and a piercing tip end attached to said ferrule.

6. A safety syringe apparatus according to claim 5, wherein said plunger, further comprises:

a shaft having a piston attached thereto, said shaft slidably engageable with said shaft seal of said syringe body;

a piston seal attached to said piston and slidably disposed within said syringe body; and a punch attached to said piston.

7. A safety syringe apparatus according to claim 6, wherein said syringe body between said shaft seal and said piston seal defines said variable vacuum compartment.

8. A safety syringe apparatus according to claim 7, wherein said syringe body further comprises a tube, a shaft seal attachment and a needle attachment, said tube of said syringe body having a shaft seal attachment end, a needle attachment end opposing said shaft seal attachment end and an inner surface extending within and along said tube between said shaft seal attachment end of said tube and said needle attachment end of said tube, said shaft seal attachment having said shaft seal interposed therein, said needle attachment having a needle receiving conduit, said shaft seal attachment and said shaft seal together insertably attachable to said shaft seal attachment end of said tube, said needle attachment insertably attachable to said needle attachment end of said tube.

9. A safety syringe apparatus according to claim 8, wherein said punch is attached to said piston and positioned adjacent said piston end of said plunger.

10. A safety syringe apparatus according to claim 8, wherein said plunger further comprises a thumb end and a piston end opposing said thumb end, a shaft slidably engageable with said shaft seal of said shaft seal attachment, a thumb platform attached to said thumb end, a piston attached to said shaft, and a punch attached to said piston, said punch positioned adjacent said piston and protruding toward said needle attachment.

11. A safety syringe apparatus according to claim 10, wherein said needle body further comprises a hollow capillary channel, said hollow capillary channel having a piercing tip end and a ferrule end opposing said piercing tip end said ferrule attached to said ferrule end of said hollow capillary channel, said piercing tip end and said hollow capillary channel slidably disposed within said needle receiving conduit of said needle attachment, said ferrule having a foundation and a grommet, said foundation having a surface, said grommet having a surface temporarily and peripherally attached to said surface of said foundation.

12. A safety syringe apparatus according to claim 11, wherein said surface of said grommet comprises means for temporarily and peripherally attaching said surface of said foundation of said ferrule to said needle attachment of said syringe body forming a slightly concave surface.

13. A safety syringe apparatus according to claim 10, wherein said piston further comprises a piston seal attached to said plunger, said piston slidably disposed, via said piston seal, against said inner surface of said tube.

14. A safety syringe apparatus according to claim 13, wherein said piston has a piston surface;

wherein said shaft seal attachment and said inner surface of said tube extending within and along said tube between said shaft seal attachment and said piston surface define a stationary surface; and wherein said stationary surface and said piston surface define said variable vacuum compartment.

15. A safety syringe apparatus according to claim 10, wherein said proximal tab is block shaped; and wherein said distal tab is wedge shaped.

16. A safety syringe apparatus according to claim 15, wherein said punch is a substantially hollow cylinder; wherein said proximal block tab extends around less than about one-half of the circumference of said substantially hollow cylinder; and wherein said distal wedge tab extends around less than about one-half of the circumference of said substantially hollow cylinder opposite said proximal block tab.

17. A method of permanently and protectively retracting a hollow needle automatically within a safety syringe apparatus, said safety syringe apparatus having a syringe body, a plunger and a needle body, the syringe body having a variable vacuum compartment and an inner surface, the plunger having a punch, said punch having internal, longitudinally offset tabs, the needle body having a ferrule and a piercing tip end, the ferrule of the needle body having a grommet and a foundation, comprising the steps of:

creating a vacuum within the variable vacuum compartment of the syringe body;

severing the grommet of the ferrule with the punch of the plunger;

frictionally engaging the foundation of the ferrule;

automatically retracting the piercing tip end of the needle body to a position within the syringe body, as a result of the vacuum created within the variable vacuum compartment;

permanently enclosing the piercing tip end of the needle body within the syringe body; and protectively pressing the piercing tip end of the needle body against the inner surface of the syringe body.

\* \* \* \* \*